(12) United States Patent
Kemp

(10) Patent No.: US 11,504,478 B2
(45) Date of Patent: Nov. 22, 2022

(54) SUBASSEMBLY FOR A DRUG DELIVERY DEVICE AND DRUG DELIVERY DEVICE

(71) Applicant: Sanofi, Paris (FR)

(72) Inventor: Thomas Mark Kemp, Ashwell (GB)

(73) Assignee: Sanofi, Paris (FR)

( * ) Notice: Subject to any disclaimer, the term of this patent is extended or adjusted under 35 U.S.C. 154(b) by 49 days.

(21) Appl. No.: 16/759,430

(22) PCT Filed: Oct. 29, 2018

(86) PCT No.: PCT/EP2018/079568
§ 371 (c)(1),
(2) Date: Apr. 27, 2020

(87) PCT Pub. No.: WO2019/086376
PCT Pub. Date: May 9, 2019

(65) Prior Publication Data
US 2020/0289760 A1    Sep. 17, 2020

(30) Foreign Application Priority Data

Nov. 3, 2017 (EP) ..................... 17306520

(51) Int. Cl.
*A61M 5/31* (2006.01)
*A61M 5/20* (2006.01)
*A61M 5/32* (2006.01)

(52) U.S. Cl.
CPC ............ *A61M 5/3137* (2013.01); *A61M 5/20* (2013.01); *A61M 5/3202* (2013.01);
(Continued)

(58) Field of Classification Search
CPC .... A61M 5/3137; A61M 5/20; A61M 5/3202; A61M 2005/3139; A61M 2205/0216;
(Continued)

(56) References Cited

U.S. PATENT DOCUMENTS

| 2,676,591 A | * | 4/1954 | Fox | ......... | A61M 5/284 |
| | | | | | 604/192 |
| 4,490,142 A | * | 12/1984 | Silvern | ......... | A61M 5/344 |
| | | | | | 604/241 |

(Continued)

FOREIGN PATENT DOCUMENTS

| CN | 2235819 | 9/1996 |
| CN | 101862489 | 10/2010 |

(Continued)

OTHER PUBLICATIONS

Dictionary.com defintion of "Elastic", https://www.dictionary.com/browse/elastic (Year: 2021).*

(Continued)

*Primary Examiner* — Theodore J Stigell
*Assistant Examiner* — Rachel T. Smith
(74) *Attorney, Agent, or Firm* — Fish & Richardson P.C.

(57) ABSTRACT

The present specification relates to a subassembly for a drug delivery device, the subassembly comprising:
  a housing adapted to contain a drug container with a needle,
  a cap, and
  a spacer,
  wherein the housing has an inner surface forming a cavity configured to retain the drug container,
  wherein the cap is configured to be releasably connected to the housing, and
  wherein the spacer is arranged between the cap and the housing.

21 Claims, 5 Drawing Sheets

(52) U.S. Cl.
CPC ............... *A61M 2005/3139* (2013.01); *A61M 2205/0216* (2013.01); *A61M 2205/586* (2013.01)

(58) Field of Classification Search
CPC .... A61M 2205/586; A61M 2005/2013; A61M 2005/3267; A61M 5/24; A61M 5/002; A61M 2005/2437; A61M 5/344
See application file for complete search history.

(56) References Cited

U.S. PATENT DOCUMENTS

| | | | | |
|---|---|---|---|---|
| 5,473,796 | A | * | 12/1995 | Fusillo ............... B65D 33/1675 24/30.5 R |
| 2012/0283645 | A1 | * | 11/2012 | Veasey ................... A61M 5/20 604/189 |
| 2014/0228767 | A1 | | 8/2014 | Nicholls et al. |
| 2015/0174325 | A1 | | 6/2015 | Young et al. |
| 2015/0273151 | A1 | * | 10/2015 | McLoughlin ......... A61M 5/002 604/66 |
| 2020/0297917 | A1 | * | 9/2020 | Helmer ............... A61M 5/3204 |

FOREIGN PATENT DOCUMENTS

| | | | |
|---|---|---|---|
| WO | WO 2017/089286 | 6/2017 | |
| WO | WO-2017089286 A1 | * 6/2017 | ............ A61M 5/001 |

OTHER PUBLICATIONS

Merriam-Webster definition "Elastic", 2022, https://www.merriam-webster.com/dictionary/elastic (Year: 2022).*
PCT International Preliminary Report on Patentability in Application No. PCT/EP2018/079568, dated May 5, 2020, 7 pages.
PCT International Search Report and Written Opinion in Application No. PCT/EP2018/079568, dated Dec. 7, 2018, 9 pages.

* cited by examiner

SUBASSEMBLY FOR A DRUG DELIVERY DEVICE AND DRUG DELIVERY DEVICE

CROSS REFERENCE TO RELATED APPLICATIONS

The present application is the national stage entry of International Patent Application No. PCT/EP2018/079568, filed on Oct. 29, 2018, and claims priority to Application No. EP 17306520.2, filed on Nov. 3, 2017, the disclosures of which are incorporated herein by reference.

TECHNICAL FIELD

The disclosure generally relates to a subassembly for a drug delivery device.

BACKGROUND

Conventionally, drug delivery devices comprise a housing or a shell in a shape of a pen which holds a drug cartridge or a drug container or a pre-filled syringe.

Administering an injection or drug is a process which presents a number of risks and challenges for users and healthcare professionals, both mental and physical. Drug delivery devices or injection devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Furthermore, the force required to push the button/plunger may be too high (e.g., if the user is elderly or a child). And, aligning the injection device, administering the injection, and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and a trigger button or other mechanism may be used to activate the injection. Autoinjectors may be single-use or reusable devices.

The drug delivery device may comprise a drive subassembly or rear subassembly and a control subassembly or front subassembly.

There is a need for an improvement of a subassembly comprising a cap removably coupled to a housing.

SUMMARY

The present disclosure relates to a subassembly and a method of assembling a subassembly.

In accordance with an aspect of the disclosure, a subassembly, e.g. a front or control subassembly for a drug delivery device is provided, wherein the subassembly comprises at least a housing, a drug container with a needle, a cap and a spacer, wherein the housing has an inner surface forming a cavity configured to retain the drug container, the cap being configured to be releasably connected to the housing, in particular at a front end of the device, and wherein the spacer is arranged between the cap and the housing or housing parts.

In an exemplary embodiment, the spacer is configured to be placed between the cap and the housing or removed therefrom in a lateral direction.

According to the disclosure, the spacer is placed in a region of a coupling section between the cap and the housing. In particular, the spacer is arranged in the region of coupling section in such a manner that the housing and the cap are spaced from each other in longitudinal direction of the subassembly, e.g. the front or control subassembly. Furthermore, the spacer may be projected beyond from the outer circumferences of the cap and the housing in a radial direction.

According to a further disclosure, the spacer comprises a cavity configured as a through hole or opening. The cavity is configured to receive at least one of a needle shield and a needle of a drug container.

In particular, the cap is positioned in such a manner by the spacer that a clearance is provided between the cap and the housing. In contrast, typically the cap is fully pressed onto the housing when the device is in its sub-assembly or assembly state which causes the cap to deflect flexible housing or needle shroud structures inwards. This allows the cap to be used to prime the device during final assembly. Further, if the device or a sub-assembly unit of the device is stored for prolonged periods there is a risk that the flexible structures will creep. The spaced arrangement of the cap in a given clearance to the housing avoids creep in either of flexible cap structures, e.g. clips, or flexible housing or needle shroud structures, e.g. needle shroud lock arms. Further, the spacer prevents the cap being fully compressed onto the housing in the sub-assembly or fully assembly state and the flexible structures, e.g. of the needle shroud, from being deflected inwards and thus avoids the risk of compromising a needle safety function.

However, in other embodiments, the spacer may be replaced by spacing elements in a packaging unit packaging the pre-assembled cap and housing. The spacing elements of the packaging act to maintain a gap between the cap and the housing or housing parts.

In a further embodiment, the spacer has a body having an inner surface forming a cavity configured to be assembled on at least one of the cap and the housing. In particular, the cavity comprises a configuration, e.g. a form, shape and/or size corresponding to the form, shape and size of at least one of the cap and the housing.

According to another embodiment, the body is formed as a clamping element. For example, the body has a curved inner surface configured to be brought into a releasable clamping engagement with the cap or the housing. The spacer may be formed as an annular clamping body which has a through cavity or opening with an overall internal contour and at least free ends formed as two clamping body elements. In particular, the body possesses a configuration substantially conforming to the shape of at least one of the cap and the housing.

In an exemplary embodiment, the curved inner surface has a friction enhancing structure and/or a friction enhancing surface. For example, the curved inner surface may comprise a profiled surface structure and/or a friction enhancing coating, textures or material can be positioned on the cap site and/or preferably on the inner surface of the spacer.

Furthermore, the body encircles at least one of a proximal end of the cap or a distal end of the housing to more than a half circle in cross-section. In particular, the spacer body is configured to have sufficient elasticity and pre-stress in its seated condition on the cap or the housing to generate a clamping force. The shapes of cap/housing and spacer body may be such that the spacer body encircles the cap or a cap part or the housing or a housing part to such an extent that locking and release prevention are created, e.g. that the spacer body encircles a generally cylindrical or tube formed cap/housing or cap/housing part to more than a half circle in cross-section as for a rings, sleeves, clamps etc.

Moreover, the spacer body may form as a clamping clip with two clamping free ends. For example, at least one of the body and the free ends is elastic. In particular, at least one of the body and the free ends is configured so as to be partially closely engaged along its length with an outer peripheral surface of the cap in a press-fit connection. Additionally, further mechanical locking structures, e.g. interlocking structures, hooks and eyes, pins and grooves, protrusions and undercuts may be used.

Furthermore, the spacer body and its mechanical attachment can be designed for permanent fixation, tool releasable fixation or preferably manually releasable fixation.

According to another aspect of the disclosure, the free ends are angled outwards. For example, the angled free ends form gripping ends configured to be gripped by a user for example for release the spacer from its clamping seat on the cap or housing.

Additionally, the spacer may have a gripping lug configured to be gripped by a user. For example, the gripping lug protrudes outwardly from an outer surface of the spacer. In particular, the gripping lug is formed as a ring-shaped mount, an eye, a protrusion with a through-hole. The gripping lug is firmly attached to or integrated in the spacer body for optional fastening of a string, a thread or a chain.

According to an exemplary embodiment, the cap has an outer surface provided with at least one of a pattern, a profiled structure, an indicator and a colour. The cap is removably coupled to the housing and adapted to prevent distal translation of the needle shroud relative to the housing.

Furthermore, the cartridge or container is prefilled with a drug, in particular an emergency drug, e.g. an allergic drug or a diabetic drug, e.g. hypoglycemia. The drug delivery device is for instance an auto-injector, a pen-injector or a syringe.

In a further embodiment, a piston or stopper slides inside the container to inject the drug. Additionally, the drug delivery device comprises an actuator mechanism for automatically injecting a patient with said drug.

According to another aspect of the disclosure, a method for assembling the control subassembly described above comprises the steps of providing a pre-assembled housing containing the drug container, the cap and the spacer and assembling the spacer onto at least one of the cap and the housing in such a manner that the cap and the housing are spaced apart from each other.

In an exemplary embodiment, the drug delivery device comprises a drive subassembly or rear subassembly and a control subassembly or front subassembly. The drive subassembly comprises a plunger, a drive spring and a rear housing part. The control subassembly may comprise a cap, a needle shroud and a front housing part. During assembly, a syringe with an attached needle and a protective needle sheath is inserted into the control subassembly in the distal direction. Afterwards, the drive subassembly is inserted into the control subassembly in the distal direction. The spacer may be releasably arranged onto a proximal end of the cap or a distal end of the housing, in particular a distal end of the front housing part.

The drug delivery device, as described herein, may be configured to inject a drug or medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle shroud, or other activation component. Activation may be a one-step or multi-step process. That is, a user may need to activate one or more activation mechanism in order to cause the automated function. For example, a user may depress a needle shroud against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1A:
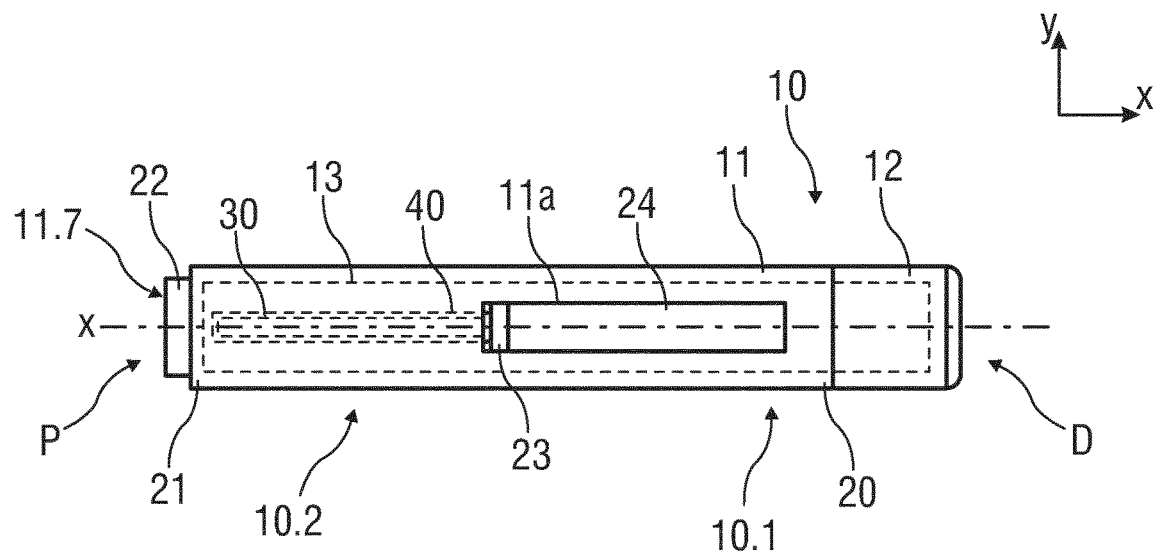
FIGS. 1A to 1B are schematic views of drug delivery devices.
Figure 1B:
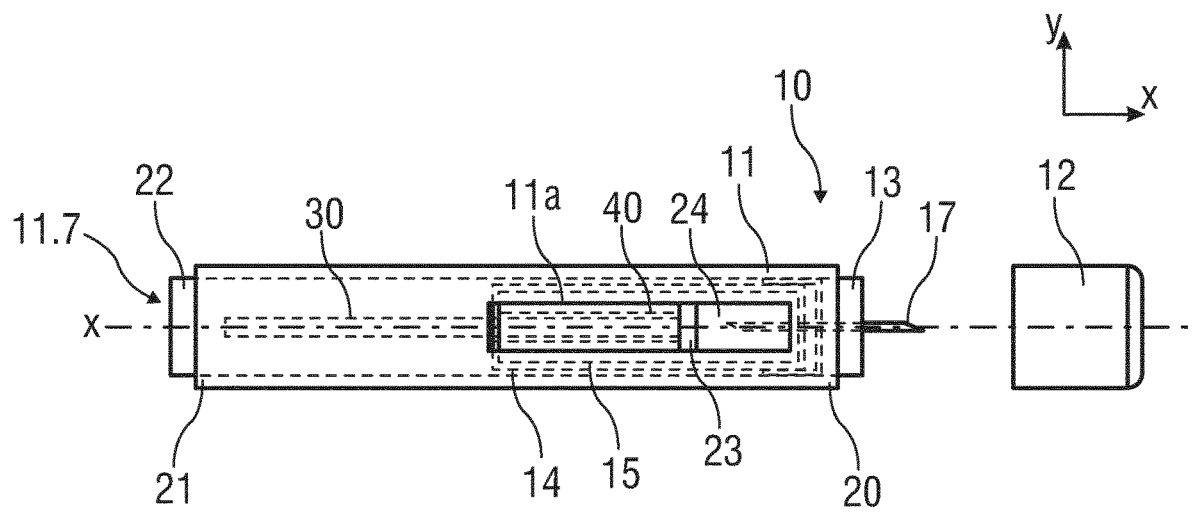

According to some embodiments of the present disclosure, an exemplary drug delivery device 10 is shown in FIGS. 1A and 1B.

Device 10, as described above, is configured to inject a drug or medicament into a patient's body.

Device 10 includes a housing 11 which typically contains a reservoir containing the medicament to be injected (e.g., a syringe 24 or a container) and the components required to facilitate one or more steps of the delivery process.

Device 10 can also include a cap assembly or a cap 12 that can be detachably mounted to the housing 11, in particular on a distal or front end D of the device 10. Typically, a user must remove cap assembly or cap 12 from housing 11 before device 10 can be operated.

As shown, housing 11 is substantially cylindrical and has a substantially constant diameter along the longitudinal axis X. The housing 11 has an inner surface 11.4 forming a cavity 11.5. The housing 11 has a distal region 20 and a proximal region 21. The term "distal" refers to a location that is relatively closer to a site of injection, and the term "proximal" refers to a location that is relatively further away from the injection site.

Device 10 can also include a needle shroud 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from distal region 20 of housing 11. Insertion of the needle 17 can occur via several mechanisms. For example, the needle 17 may be fixedly located relative to housing 11 and initially be located within an extended needle shroud 13. Proximal movement of the sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to housing 11. Such insertion can be triggered by movement of sleeve 13 or by another form of activation, such as, for example, a button 22. As shown in FIGS. 1A & 1B, button 22 is located at a proximal or back end P of the housing 11. However, in other embodiments, button 22 could be located on a side of housing 11. In further embodiments, the button 22 has been deleted and is replaced for instance by a sleeve trigger mechanism, e.g. provided by pushing the needle shroud 13 inside the housing when the drug delivery device is put onto an injection side.

Other manual or automated features can include drug injection or needle retraction, or both. Injection is the process by which a bung or piston 23 is moved from a proximal location within a container or syringe 24 to a more distal location within the syringe 24 in order to force a medicament from the syringe 24 through needle 17.

In some embodiments, an energy source, e.g. a drive spring 30 is arranged in a plunger 40 and is under compression before device 10 is activated. A proximal end of the drive spring 30 can be fixed within proximal region 21 of housing 11, and a distal end of the drive spring 30 can be configured to apply a compressive force to a proximal surface of piston 23. Following activation, at least part of the energy stored in the drive spring 30 can be applied to the proximal surface of piston 23. This compressive force can act on piston 23 to move it in a distal direction. Such distal movement acts to compress the liquid medicament within the syringe 24, forcing it out of needle 17.

Following injection, the needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe 24 to move it in a proximal direction. Following sufficient retraction, any relative movement between the needle 17 and the housing 11 can be locked with a locking mechanism. In addition, button 22 or other components of device 10 can be locked as required.

In some embodiments, the housing may comprise a window 11a through which the syringe 24 can be monitored.

The drug delivery device 10 may be divided in two subassemblies, a front or control subassembly 10.1 and a drive subassembly 10.2. This allows for improving flexibility as to the time and location of manufacture of the subassemblies and final assembly with the syringe 24.

Figure 6:
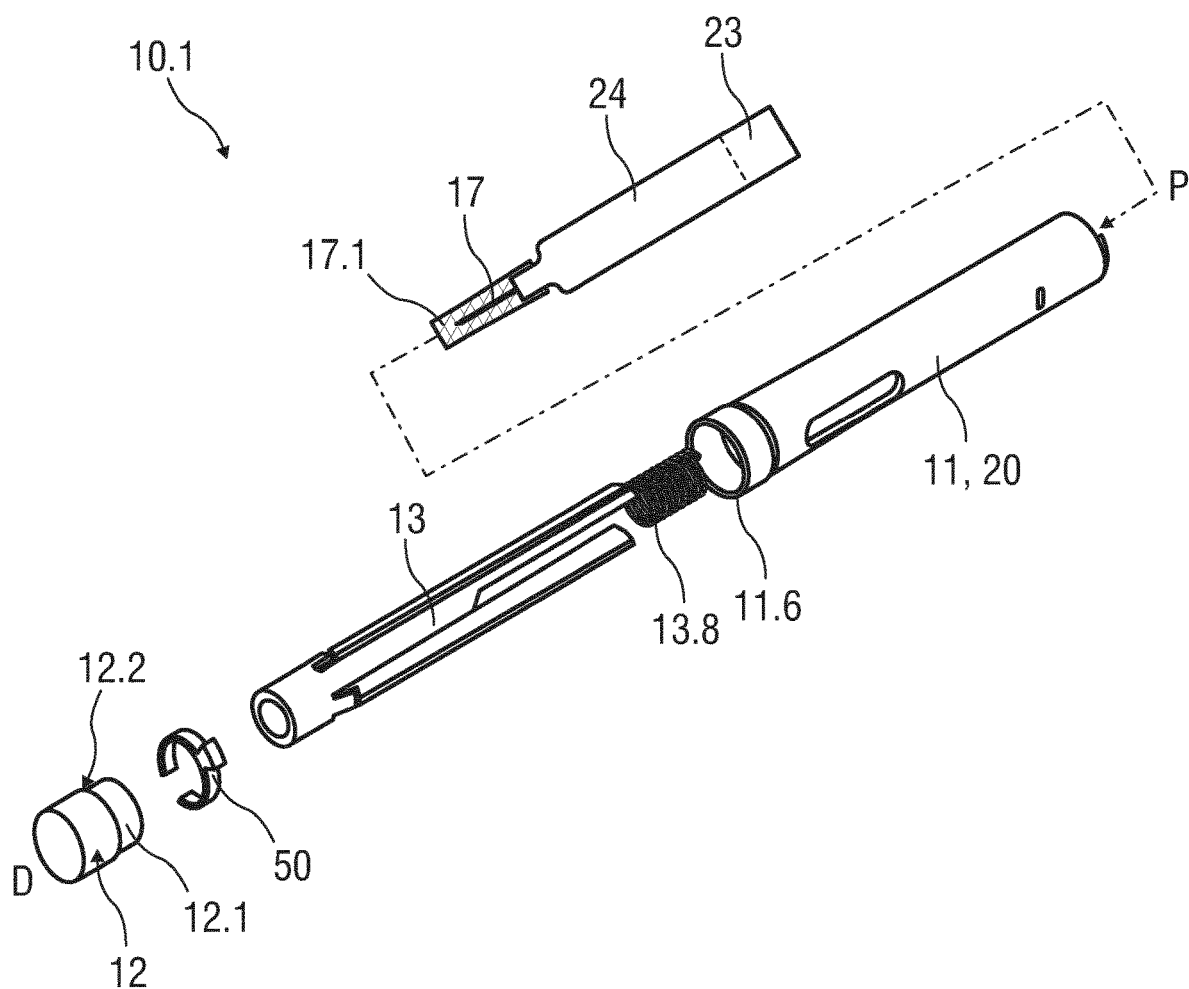
FIG. 6 is a schematic exploded view of a subassembly, e.g. a front or control subassembly.

The front or control subassembly 10.1 may comprise the distal region 20 of the housing 11, the cap 12 and optionally a needle shroud 13 and a shroud spring 13.8 (cf. FIG. 6). The rear or drive subassembly 10.2 may comprise the plunger 40 and the drive spring 30 and a rear housing part 11.7.

Figure 2A:
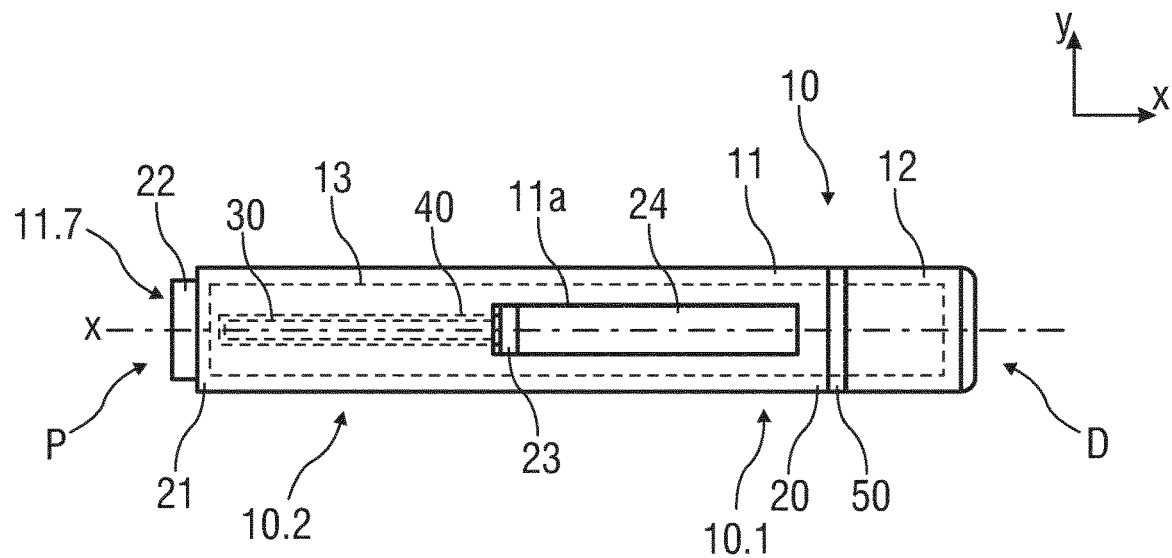
FIG. 2A is a schematic view of a drug delivery device with a spacer arranged between a cap and a housing of the device.

FIG. 2A is a schematic view of a drug delivery device 10, in particular one of the device described above, with a spacer 50 arranged between the cap 12 and the housing 11.

In particular, due to the positioning of the spacer 50, the cap 12 is positioned in such a manner that a clearance is provided between the cap 12 and the housing 11.

This allows the cap 12 to be used to prime the device 10 during sub-assembly or final assembly. The spaced arrangement of the cap 12 in a given clearance to the housing 11 avoids creep in either of flexible cap structures, e.g. clips, or flexible housing or needle shroud structures.

The spacer 50 prevents the cap 12 being fully compressed onto the housing 11 in the sub-assembly state and the flexible structures, e.g. of the needle shroud 13, from being deflected inwards and thus avoids the risk of compromising a needle safety function.

However, in alternative embodiments, the spacer 50 may be replaced by spacing elements in a packaging unit packaging the pre-assembled cap 12 and housing 11. The spacing elements of the packaging act to maintain a gap between the cap 12 and the housing 11 or housing parts (not shown).

The spacer 50 may be configured to be placed between the cap 12 and the housing 11 or housing part 20 in a lateral direction, i.e. in a direction substantially radially towards the longitudinal axis X. Likewise, the spacer 50 may be configured to be removed from between the cap 12 and the housing 11 or housing part 20 in a lateral direction, i.e. in a direction substantially radially away from the longitudinal axis X.

Figure 2B:
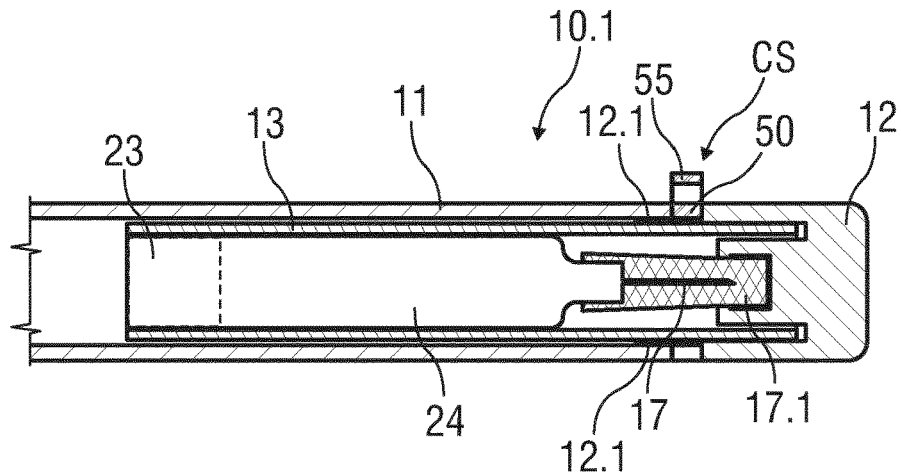
FIG. 2B is a schematic sectional view of the drug delivery device with the spacer.

FIG. 2B shows is a partial schematic sectional view of a subassembly configured as a front or control subassembly 10.1 of drug delivery device 10 with the spacer 50. The front or control subassembly 10.1 comprises at least the housing 11, the needle shroud 13, a pre-filled syringe, e.g. a cartridge 24 with piston 23 and needle 17 covered by a needle shield 17.1 and the removable cap 12 configured to grip the needle shield 17.1.

The spacer 50 is placed in a region of a coupling section CS between the cap 12 and the housing 11. In particular, the spacer 50 is arranged in the region of coupling section CS in such a manner that the housing 11 and the cap 12 are spaced from each other in longitudinal direction of the control subassembly 10.1. Furthermore, the spacer 50 may be projected beyond from the outer circumferences of the cap 12 and the housing 11 in a radial direction.

Figure 2C:
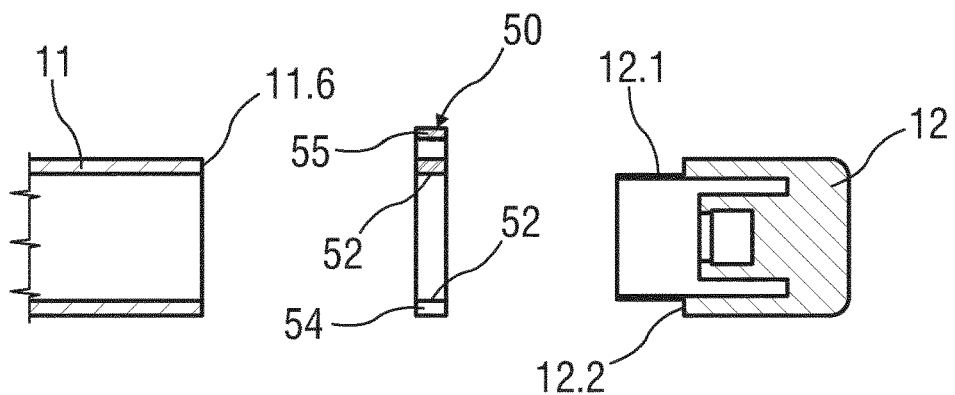
FIG. 2C is an exploded view of the housing, the spacer and the cap.

FIG. 2C shows an exploded view of the housing 11, the spacer 50 and the cap 12. The spacer 50 comprises a cavity 53 configured as a through-hole or opening. The spacer 50 is configured as an annular, in particular ring-segmented clamping body. The cap 12 comprises a proximal end 12.1 configured as a projection extending form the cap 12 in to the proximal direction. The proximal end 12.1 has a ring-shape or cylindrical shape. The diameter of the proximal end 12.1 is less than the outer diameter of the cap 12 and the outer diameter as well as the inner diameter of the housing 11. In particular, the proximal end 12.1 and the distal end of the housing 11 may be partially overlapped each other.

The spacer 50 is arranged onto the proximal end 12.1 between an end face 12.2 of the cap 12 and an end face 11.6 of the housing 11. The end faces 12.2, 11.6 are spaced apart from each other by the spacer 50.

Figure 3:
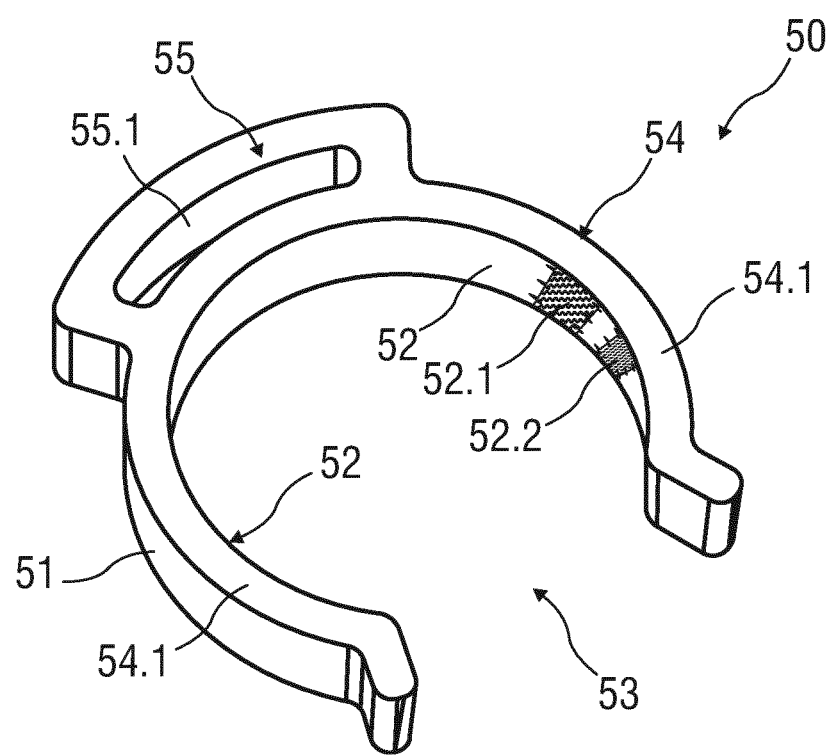
FIG. 3 is a schematic perspective view of a spacer.

FIG. 3 is a schematic perspective view of an exemplary embodiment of a spacer 50.

The spacer 50 has a body 51 having an inner surface 52. The inner surface 52 forms a cavity 53 configured to be assembled on the cap 12. Alternatively, the spacer 50 may be attached onto the housing 11 (not shown).

The cavity 53 has a configuration, e.g. a form, shape and/or size corresponding to the form, shape and size of the cap 12.

Furthermore, the body 51 is formed as a clamping element 54. For example, the body 51 has an inner surface 52 which is curved and configured to be brought into a releasable clamping engagement with the cap 12.

The curved inner surface 52 can include a friction enhancing structure 52.1, e.g. a grooved or ribbed surface or a texture. Alternatively or additionally, the inner surface 52 may comprise a friction enhancing surface 52.2, e.g. a coating or material. Further, a profiled surface structure and/or a friction enhancing coating, textures or material can be positioned on the outer site of the cap 12.

For example, the body 51 furthermore comprises a configuration which encircles a proximal end 12.1 of the cap 12. In particular, the body 51 encircles the proximal cap end 12.1 to more than a half circle in cross-section, for example more than 180°.

Furthermore, the spacer body 51 is configured to have sufficient elasticity and pre-stress in its seated condition on the cap 12 to generate a clamping force.

In particular, the spacer body 51 is formed as a clamping clip or element 54 with two clamping free ends 54.1. In a possible embodiment, the clamping free ends 54.1 are elastic. In other embodiments, the body 51 as well as the free ends 54.1 are elastic. For example, the spacer 50 may be formed as an elastic plastic part, e.g. a one component injection moulding part. Alternatively, the spacer 50 is formed as a two component injection moulding part with a rigid body part and elastic clamping end parts.

The body 51 and the free ends 54.1 are configured to be partially closely engaged with an outer peripheral surface of the cap 12 in a press-fit or clamping connection.

To grip the spacer 50 for assembling or disassembling, the free ends 54.1 are angled outwards. For example, the angled free ends 54.1 form gripping ends 54.2 configured to be gripped by a user for example to release the spacer 50 from its clamping seat on the cap 12.

Additionally, the spacer 50 may have a gripping lug 55 configured to be gripped by a user. The gripping lug 55 protrudes radially outwards from the outer surface of the spacer 50. The gripping lug 55 is formed as a protrusion with a through-hole 55.1. Alternatively, the gripping lug 55 may be formed as a ring-shaped mount or a gripping eye.

Figure 4:
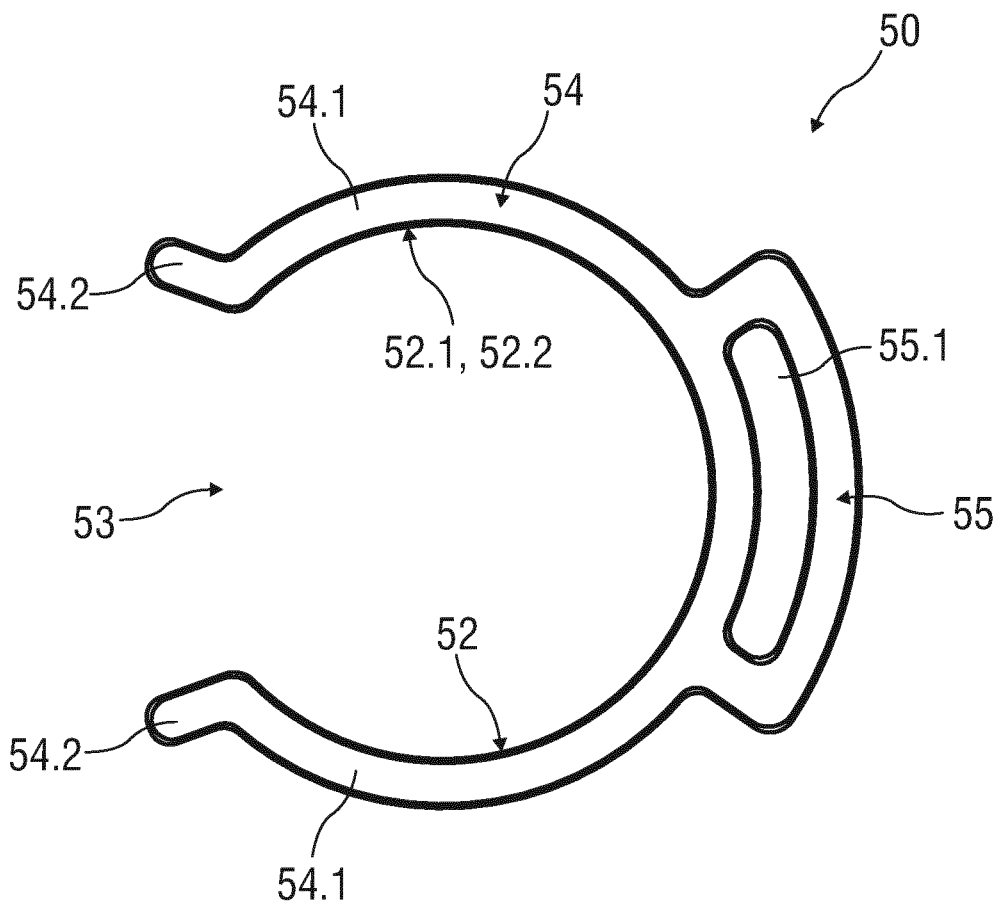
FIG. 4 is a schematic sectional view of a spacer.
Figure 5:
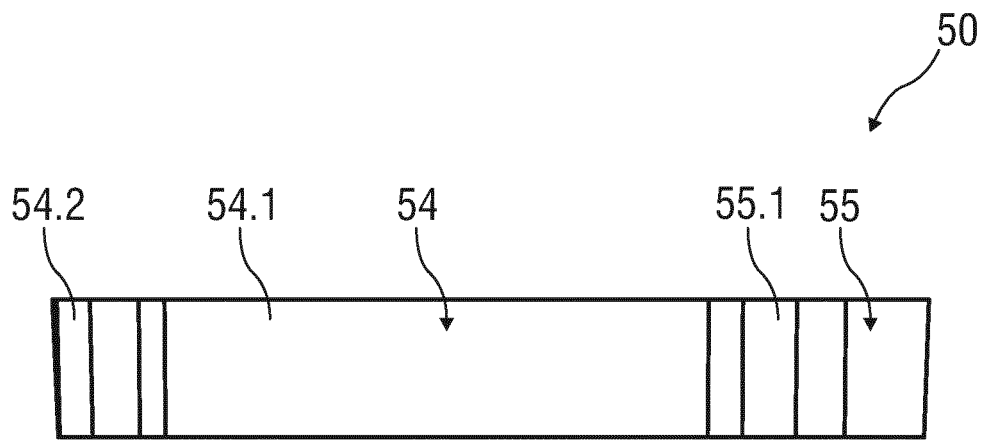
FIG. 5 is a side view of a spacer.

FIG. 4 is a schematic sectional view of the spacer 50 and FIG. 5 is a side view of the spacer 50.

FIG. 6 shows an exploded view of the front or control subassembly 10.1 comprising at least the housing 11, the needle shroud 13, a pre-filled syringe having the cartridge 24 with the piston 23 and the needle 17 covered by the needle shield 17.1, the spacer 50 and the cap 12. The spacer 50 comprises as through opening the cavity 53 which is configured to receive at least one of a needle shroud 13 and the needle shield 17.1. Furthermore, the cavity 53 is configured to be assembled on a proximal end 12.1, e.g. a projection, of the cap 12.

The spacer 50 may be formed as an annular clamping body or clamping element 54 which has the through cavity 53 with an overall or circular-segmented internal contour or inner surface 52 and at least the two free ends 54.1 formed as two clamping body elements.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 10 drug delivery device
10.1 control subassembly
10.2 drive subassembly
11 housing
11.1 stop
11.2 lug
11.3 recess
11.4 inner surface
11.5 cavity
11.6 end face
11.7 rear housing part
11a window
12 cap
12.1 proximal end
12.2 end face
13 needle shroud
13.1 shroud body
13.2 inner surface
13.3 cavity
13.4 shroud beam
13.5 radial support surface
13.6 opening
13.7 open end
13.8 shroud spring
13.9 distal front end
13.10 retaining slot
17 needle
17.1 needle shield
20 distal region of the drug delivery device
21 proximal region of the drug delivery device
22 button
23 piston
24 cartridge
30 energy source, e.g. drive spring
40 plunger
50 spacer
51 body
52 inner surface
53 cavity
54 clamping element
54.1 free end
54.2 gripping end
55 gripping lug
55.1 through-hole
CS coupling section

The invention claimed is:

1. A subassembly for a drug delivery device, the subassembly comprising:
a housing;
a drug container with a needle contained within the housing;
a cap; and a spacer,
wherein the housing has an inner surface forming a cavity configured to retain the drug container,
wherein the cap is configured to be releasably connected to the housing,
wherein the spacer is arranged between the cap and the housing when the cap is releasably connected to the housing, and
wherein the spacer is configured to be removed from between the cap and the housing in a lateral direction, wherein the lateral direction corresponds to a direction substantially radially away from the longitudinal axis of the subassembly.

2. The subassembly according to claim 1, wherein the spacer is configured to be placed between the cap and the housing in the lateral direction.

3. The subassembly according to claim 1, wherein the spacer has a body having an inner surface forming a spacer cavity configured to be assembled on at least one of the cap or the housing.

4. The subassembly according to claim 3, wherein the spacer cavity comprises a configuration corresponding to at least one of a form, a shape, or a size of at least one of the cap or the housing.

5. The subassembly according to claim 3, wherein the body is formed as a clamping element.

6. The subassembly according to claim 5, wherein the clamping element is formed as a clip comprising two clamping free ends.

7. The subassembly according to claim 6, wherein at least one of the body or the two clamping free ends is elastic.

8. The subassembly according to claim 6, wherein the two clamping free ends are angled outward.

9. The subassembly according to claim 3, wherein the body has a curved inner surface configured to be brought into a releasable clamping engagement with the cap or the housing.

10. The subassembly according to claim 9, wherein the curved inner surface has a friction enhancing structure and/or a friction enhancing surface.

11. The subassembly according to claim 3, wherein the body, in a cross-section, encircles at least half of at least one of a proximal end of the cap or a distal end of the housing.

12. The subassembly according to claim 1, wherein the spacer has a gripping lug configured to be gripped by a user.

13. The subassembly according to claim 12, wherein the gripping lug protrudes outwardly from an outer surface of the spacer and/or is formed as at least one of a ring-shaped mount, an eye, or a protrusion with a through-hole.

14. The subassembly according to claim 1, wherein the drug container is prefilled with a drug.

15. The subassembly according to claim 1, wherein the spacer is removable from the subassembly to allow a user to prime the drug delivery device by pressing the cap onto the housing.

16. A method comprising:
providing a pre-assembled housing;
arranging a drug container within the housing;
providing a cap;
providing a spacer; and
assembling a subassembly by placing the spacer onto at least one of the cap or the housing in such a manner that the cap and the housing are spaced apart from each other,
wherein the spacer is configured to be removed from between the cap and the housing in a lateral direction, wherein the lateral direction corresponds to a direction substantially radially away from the longitudinal axis of the subassembly.

17. The method according to claim 16, wherein the spacer is releasably arranged onto a proximal end of the cap.

18. The method according to claim 16, wherein the subassembly is a control subassembly, and the method further comprises inserting a drive subassembly into the control subassembly.

19. The method according to claim 16, wherein placing the spacer onto at least one of the cap or the housing comprises releasably arranging the spacer onto a proximal end of the cap or a distal end of the housing.

20. The method according to claim 16, wherein placing the spacer onto at least one of the cap or the housing comprises placing the spacer on at least one of the cap or the housing such that the spacer can be removed from the subassembly to allow a user to prime a drug delivery device comprising the subassembly by pressing the cap onto the housing.

21. A drug delivery device, comprising:
a subassembly, the subassembly comprising:
    a housing;
    a drug container with a needle contained within the housing;
    a cap; and
    a spacer,
    wherein the housing has an inner surface forming a cavity configured to retain the drug container,
    wherein the cap is configured to be releasably connected to the housing, and
    wherein the spacer is arranged between the cap and the housing when the cap is releasably connected to the housing,
    wherein the spacer is configured to be removed from between the cap and the housing in a lateral direction, wherein the lateral direction corresponds to a direction substantially radially away from the longitudinal axis of the subassembly.

* * * * *